United States Patent [19]
Madsen et al.

[11] Patent Number: 6,040,134
[45] Date of Patent: Mar. 21, 2000

[54] METHOD OF DIAGNOSING PRECLINICAL DIABETES

[75] Inventors: Ole Dragsbaek Madsen, Soborg; Birgitte Koch Michelsen, Lyngy; Jacob Steen Petersen, Copenhagen, all of Denmark; Bart O. Roep, Leiden, Netherlands; Borge Teisner, Odense, Denmark

[73] Assignee: Novo Nordisk A/S, Bagsvaerd, Denmark

[21] Appl. No.: 08/892,783

[22] Filed: Jul. 15, 1997

Related U.S. Application Data

[63] Continuation of application No. PCT/DK96/00050, Jan. 31, 1996.

[30] Foreign Application Priority Data

Jan. 31, 1995 [DK] Denmark .................. 0109/95

[51] Int. Cl.$^7$ .......................... G01N 33/50; G01N 33/53; G01N 33/564; G01N 33/567
[52] U.S. Cl. .................... 435/4; 435/6; 435/7.1; 435/7.2; 435/7.24; 435/965; 435/975; 435/7.7; 435/7.72; 435/7.9; 435/7.92; 435/372.3; 436/503; 436/506; 436/63; 530/350; 530/395; 530/387.1; 530/391.3
[58] Field of Search .......................... 435/975, 7.1, 7.24, 435/7.7, 7.72, 7.92, 7.93, 7.95, 7.94, 965, 4, 6, 7.2, 372.3; 436/503, 506, 63; 530/350, 395, 387.1, 391.3

[56] References Cited

U.S. PATENT DOCUMENTS 5,674,692 10/1997 Baekkeskov et al. .

FOREIGN PATENT DOCUMENTS

WO 91/17186 11/1991 WIPO .
WO 94/24564 10/1994 WIPO .

OTHER PUBLICATIONS

Arden, S.D. et al. Imogen38: A novel 38–kD islet mitochondrial autoantigen recognized by T cells from a newly diagnosed type 1 diabetic patient. J. Clin. Invest., 97(2): 551–561, Jan. 1997.

Aanstoot, H. et al. Identification and characterization of Glima 38, a glycosylated islet cell membrane antigen, which together with GAD65 and IA2 marks the early phases of autoimmune response in Type I diabetes. J. Clin. Invest., 97(12): 2772–2783, Jun. 1997.

Jensen CH, et al., Eur J Biochem, accession No. 95010145, 1;222(1): 83–92 (Oct. 1994).

Jensen CH, et al., Hum Reprod, accession No. 93273893, 8(4): 635–41 (Apr. 1993).

Tornehave D, et al., Anat Embryol (Berl), accession No. 93289978, 187(4): 335–41 (Apr. 1993).

Laborda J, et al., J Biol Chem, accession No. 93179372, 25;268(6): 3817–20 (Feb. 1993).

Kundig, et al., Proc. Natl. Acad. Sci., vol. 89, pp. 7757–7761 (Aug. 1992).

Christgau, et al., The Journal Of Biological Chemistry, vol. 266, No. 31, pp. 21257–21264 (Nov. 1991).

*Primary Examiner*—Nancy A Johnson
*Assistant Examiner*—Anne L. Holleran
*Attorney, Agent, or Firm*—Steve T. Zelson, Esq.; Reza Green, Esq.

[57] ABSTRACT

The present invention relates to a method of diagnosing preclinical insulin-dependent diabetes mellitus by determining the T cell response to a specific islet cell antigen fetal antigen 1 (FA1) or the presence of autoantibodies against FA1 in serum, a test kit for use in the method, as well as a pharmaceutical composition of FA1 and a method for use of the pharmaceutical composition for therapy of insulin-dependent diabetes mellitus.

8 Claims, 2 Drawing Sheets

METHOD OF DIAGNOSING PRECLINICAL DIABETES

CROSS-REFERENCE TO RELATED APPLICATIONS

This application is a continuation of PCT/DK96/00050 filed Jan. 31, 1996 which claims priority under 35 U.S.C. 119 of Danish application 0109/95 filed Jan. 31, 1995, the contents of which are fully incorporated herein by reference.

FIELD OF INVENTION

The present invention relates to a method of diagnosing preclinical stages of insulin-dependent diabetes mellitus by determining the T cell response to a specific islet cell antigen or the presence of autoantibodies against a specific islet cell antigen in serum, a test kit for use in the method, as well as the use of the islet cell antigen in therapy and a pharmaceutical composition for said use.

BACKGROUND OF THE INVENTION

Insulin-dependent diabetes mellitus (IDDM) is an autoimmune disease characterized by the gradual destruction of the insulin-producing pancreatic islet β-cells. Clinical symptoms of diabetes set in at a fairly late stage of this process, at a point where about 90% of the β-cells have been destroyed. However, in recent years it has been found that a number of circulating autoantibodies against β-cells associated with IDDM are present in serum before the clinical onset of the disease. Such circulating autoantibodies include one against a 64 kD islet β-cell autoantigen (S. Baekkeskov et al., *Nature* 298, 1982, pp. 167–169). The 64 kD autoantibody has been found to be present in the serum of more than 80% of the patients with newly diagnosed IDDM and has furthermore been found in serum up to several years before the clinical onset of the disease (S. Baekkeskov et al., *J. Clin. Invest.* 79, 1987, pp. 926–934; M. R. Atkinson et al., *Lancet* 335, 1990, pp. 1357–1360; E. Sigurdsson and S. Baekkeskov, *Curr. Top. Microbiol. Immun.* 164, 1990, pp. 143–167). The early detection of the 64 kD autoantibody would be of great value for the study of the development of IDDM as well as for devising preventive therapies.

The 64 kD autoantigen has been identified (S. Baekkeskov et al., *Nature* 347, 1990, pp. 151–156) as the enzyme glutamic acid decarboxylase (GAD) which is otherwise known to be involved in the biosynthesis of gamma-amino butyric acid in the central nervous system. The use of GAD for the diagnosis of preclinical IDDM has been suggested in WO 92/04632 and WO 92/05446.

A 38 kD β-cell antigen recognised by a T cell clone isolated from the blood of a recently diagnosed IDDM patient is described in WO 91/17186. It is suggested to use the antigen in the diagnosis or therapy of IDDM.

SUMMARY OF THE INVENTION

It has surprisingly been found that an antigen originally isolated from amniotic fluid and known as fetal antigen 1 is recognized by T cells from newly diagnosed IDDM patients. Experiments have established that the antigen does not react with T cells of patients with long-established IDDM or with the T cells of healthy controls. Detection of T cell response to GAD or the 38 kD β-cell antigen disclosed in WO 91/17186 may be indicative of preclinical IDDM, but such response can also be found in healthy subjects and is not found in all individuals that develops IDDM.

Accordingly, the present invention relates to a method of diagnosing preclinical insulin-dependent diabetes mellitus (IDDM), the method comprising contacting fetal antigen 1 (FA1) with T cells of a subject to be diagnosed for preclinical IDDM and detecting any T cell response to the FA1, such a response being indicative of preclinical IDDM in the subject.

The method is useful for diagnosing and/or monitoring the development of preclinical stages of IDDM in a patient and thus presents a valuable opportunity to initiate preventive or ameliorative treatment of IDDM.

FA1 was originally isolated from human amniotic fluid (cf. T. N. Fay et al., *Eur. J. Obstet. Gynecol. Reprod. Biol.* 29, 1988, pp. 73–85. The presence of FA1 in fetal pancreatic tissue and in islet β-cells of adult pancreatic tissue is reported in D. Tornehave et al., *Anat. Embryol.* 187, 1993, pp. 335–341. FA1 has been characterized as a single-chain glycoprotein with a molecular weight of 32–38 kD. The amino acid composition and 37 N-terminal amino acids of the protein appear from C. H. Jensen et al., *Human Reproduction* 8, 1993, pp. 635–641. The protein has been further characterized and shown to be located in the β-cell granules. Furthermore, the complete amino acid sequence is shown in C. H. Jensen et al., *Eur. J. Biochem.* 225, 1994, pp. 83–92. Human FA1 has been found to 99% identical to a translated human dlk mRNA isolated from the adrenal gland (cf. Laborda et al., *J. Biol. Chem.* 268, 1993, pp. 3817–3820; GenBank/EMBL accession number Z12171). It is therefore aasumed that the protein is is the post-translationally modified gene product of the human dlk mRNA.

In another aspect, the present invention relates to a method of determining the presence of autoantibodies against fetal antigen 1 (FA1 autoantibodies) in serum, which method comprises contacting a serum sample with FA1 or a fragment thereof capable of binding FA1 autoantibodies, and detecting any binding of autoantibodies to the FA1.

In a further aspect, the invention relates to a test kit for determining the presence of FA1 autoantibodies in serum, which comprises, in separate containers, (a) fetal antigen 1 immobilized on a solid support, and
(b) a labelled reagent capable of binding to FA1 autoantibodies.

Alternatively, the present invention relates to a test kit for determining the presence of FA1 autoantibodies in serum, which comprises, in separate containers, (a) fetal antigen 1 immobilized on a solid support, and
(b) a labelled antibody which is capable of competing with the FA1 autoantibody for binding to FA1.

DETAILED DISCLOSURE OF THE INVENTION

Figure 1:
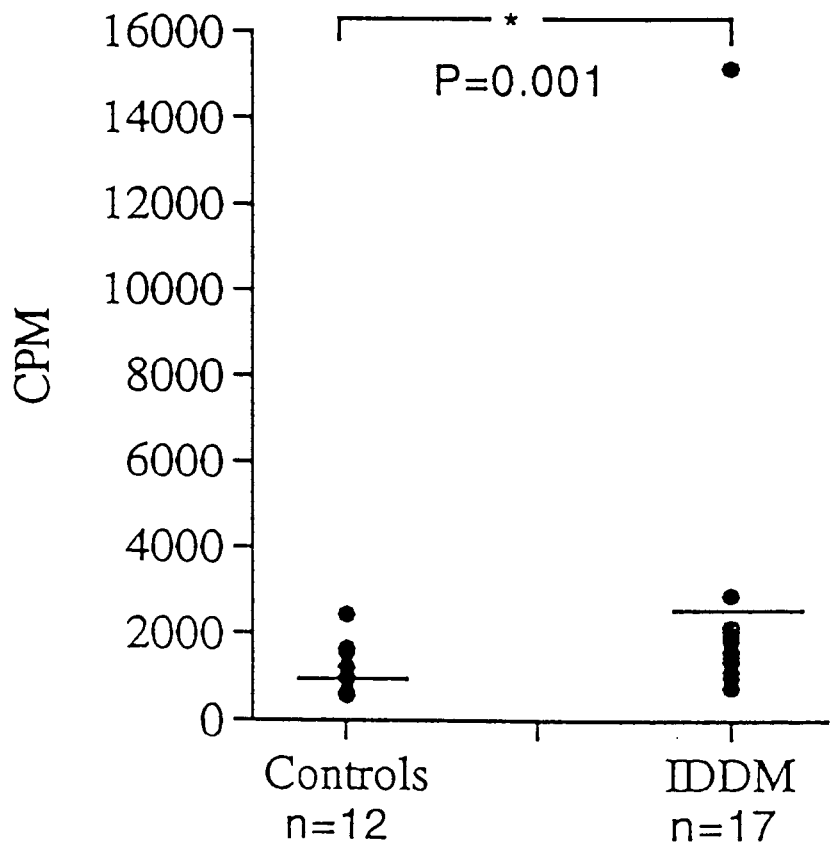
FIG. 1 is a graphic illustration of immunoprecipitation of $^{125}$I-labelled FA1 using sera from control patients and those with insulin-dependent diabetes mellitus (IDDM).

FA1 has been found to be present in fetal pancreas, liver and adrenal cortex, and in the pancreatic β-cells and adrenal cortex of adults. It is assumed that FA1s from these tissues are sufficiently homologous to be useful in the present method regardless of their origin. However, it may be preferred to use pancreatic FA1 for the purpose of diagnosing IDDM or a preclinical stage thereof in patient serum. Likewise, it is contemplated that FA1 derived from different mammalian sources, such as cattle, pigs, rats, mice, dogs or cats, may be used in the present method. For the purpose of diagnosing IDDM in a human patient it will, however, typically be preferred to use FA1 derived from a human source.

The FA1 employed for the present purposes may be in different forms, e.g. in the form of a pre-pro-peptide, a pro-peptide, various processed forms thereof, mature FA1 or various glycosylated forms thereof (e.g. as described in C. H. Jensen et al., Eur. J. Biochem. 225, 1994, pp. 83–92, vide specifically FIG. 2). Allelic variants of FA1, i.e. an altered FA1 protein encoded by a mutated gene, but having substantially the same activity as the FA1 described in C. H. Jensen et al., supra, are also included in the scope of the present invention. Furthermore, fragments of FA1 which are capable of reacting with T cells of prediabetic patients or with FA1 autoantibodies of prediabetic patients are intended to be included within the scope of the present invention.

In addition, homologues of FA1 may be employed provided that they are capable of reacting with T cells of prediabetic patients or with FA1 autoantibodies of prediabetic patients. A homologue of FA1 may, in the present context, be defined as a protein comprising an amino acid sequence exhibiting a degree of identity of at least about 60% with the amino acid sequence of FA1. The degree of identity may be determined by conventional methods, see for instance, Altshul et al., Bull. Math. Bio. 48: 603–616, 1986, and Henikoff and Henikoff, Proc. Natl. Acad. Sci. USA 89: 10915–10919, 1992. Briefly, two amino acid sequences are aligned to optimize the alignment scores using a gap opening penalty of 10, a gap extension penalty of 1, and the "blosum 62" scoring matrix of Henikoff and Henikoff, supra.

Alternatively, the FA1 homologue may be one encoded by a nucleotide sequence hybridizing with an oligonucleotide probe prepared on the basis of the nucleotide sequence encoding FA1 under conditions using approximately 2×SSC and a hybridization temperature of about 50° C.

FA1 homologues may have one or more amino acid substitutions, deletions or additions. These changes are preferably of a minor nature, including conservative amino acid substitutions that do not significantly affect the folding or activity of the protein, small deletions, small amino- or carboyxyl-terminal extensions, such as an amino-terminal methionine residue. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

It will be apparent to persons skilled in the art that such substitutions may be made outside the regions critical to the function of the molecule without impairing the activity of the resulting FA1 homologue. Amino acids essential to the activity of the polypeptide of the invention, and therefore preferably not subject to substitution, may be identified according to procedures known in the art, such as site-directed mutagenesis or alanine-scanning mutagenesis (Cunningham and Wells, Science 244, 1081–1085, 1989). In the latter technique mutations are introduced at every residue in the molecule, and the resulting mutant molecules are tested for FA1 activity to identify amino acid residues that are critical to the activity of the molecule.

A FA1 homologue may be isolated by preparing a genomic or cDNA library of a cell of the species or tissue in question, and screening for DNA sequences coding for all or part of the homologue by using synthetic oligonucleotide probes in accordance with standard techniques, e.g. as described by Sambrook et al., Molecular Cloning:A Laboratory Manual, 2nd. Ed. Cold Spring Harbor Laboratory, Cold Spring Harbor, N.Y., 1989, or by means of polymerase chain reaction (PCR) using specific primers as described in, e.g. PCR Protocols, 1990, Academic Press, San Diego, Calif., USA.

The FA1 employed in the method of the present invention may be produced by extraction from tissues containing it, but it is preferred to produce it by recombinant DNA techniques in a manner known per se. A DNA sequence encoding FA1 suitably be of obtained by preparing a genomic or cDNA library and screening for DNA sequences coding for all or part of the FA1 by hybridization using synthetic oligonucleotide probes in accordance with standard techniques (cf. Sambrook et al., supra). The probes may suitably be prepared on the basis of the published amino acid sequence of FA1. For the present purpose, the DNA sequence encoding the FA1 is preferably of human origin i.e. derived from a human genomic DNA or cDNA library.

The DNA sequence encoding the FA1 may also be prepared synthetically by established standard methods, e.g. the phosphoamidite method described by Beaucage and Caruthers, Tetrahedron Letters 22 (1981), 1859–1869, or the method described by Matthes et al., EMBO Journal 3 (1984), 801–805. According to the phosphoamidite method, oligonucleotides are synthesized, e.g. in an automatic DNA synthesizer, purified, annealed, ligated and cloned in suitable vectors.

The DNA sequence encoding FA1 may also be prepared by polymerase chain reaction using specific primers, for instance as described in U.S. Pat. No. 4,683,202, Saiki et al., Science 239 (1988), 487–491, or PCR Protocols, 1990, Academic Press, San Diego, Calif., USA. Suitable PCR primers may, for instance, be prepared on the basis of the published dlk mRNA sequence described by Laborda et al., supra.

The DNA sequence encoding FA1 may be introduced into host cells on a recombinant vector which may be any vector which may conveniently be subjected to recombinant DNA procedures. The choice of vector will often depend on the host cell into which it is to be introduced. Thus, the vector may be an autonomously replicating vector, i.e. a vector which exists as an extra chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the FA1 is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the FA1.

The promoter may be any DNA sequence which shows transcriptional activity in the host cell of choice and may be derived from genes encoding proteins either homologous or heterologous to the host cell.

The host cell into which the DNA construct or the recombinant vector of the invention is introduced may be any cell which is capable of producing the present polypeptide and includes bacteria, yeast, fungi and higher eukaryotic cells. However, to provide correct glycosylation of FA1, the host cell is preferbly a mammalian cell.

Examples of suitable mammalian cell lines are the COS (e.g. ATCC CRL 1650), BHK (e.g. ATCC CRL 1632, ATCC CCL 10), CHL (e.g. ATCC CCL39) or CHO (e.g. ATCC CCL 61) cell lines. Methods of transfecting mammalian cells and expressing DNA sequences introduced in the cells are described in e.g. Kaufman and Sharp, *J. Mol. Biol.* 159 (1982), 601–621; Southern and Berg, *J. Mol. Appl. Genet.* 1 (1982), 327–341; Loyter et al., *Proc. Natl. Acad. Sci. USA* 79 (1982), 422–426; Wigler et al., *Cell* 14 (1978), 725; Corsaro and Pearson, *Somatic Cell Genetics* 7 (1981), 603, Graham and van der Eb, *Virology* 52 (1973), 456; and Neumann et al., *EMBO J.* 1 (1982), 841–845.

Examples of suitable promoters for directing the transcription of the DNA encoding the polypeptide of the invention in mammalian cells are the SV40 promoter (Subramani et al., *Mol. Cell Biol.* 1 (1981), 854–864), the MT-1 (metallothionein gene) promoter (Palmiter et al., *Science* 222 (1983), 809–814) or the adenovirus 2 major late promoter.

The DNA sequence encoding the FA1 may also, if necessary, be operably connected to a suitable terminator, such as the human growth hormone terminator (Palmiter et al., op. cit.). The vector may further comprise elements such as polyadenylation signals (e.g. from SV40 or the adenovirus 5 Elb region), transcriptional enhancer sequences (e.g. the SV40 enhancer) and translational enhancer sequences (e.g. the ones encoding adenovirus VA RNAs).

Transfected host cells may then be cultured in a suitable nutrient medium under conditions permitting the expression of the FA1 which is subsequently recovered from the culture. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection).

The FA1 produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel-filtration chromatography, affinity chromatography, or the like.

In the method according to the invention, the T cell response to FA1 may be determined by measuring the proliferation of T cells, e.g. in a lymphocyte stimulation assay as described in B.O. Roep et al., "T cell reactivity to β-cell membrane antigen associated with β-cell destruction", Diabetes, in press, using FA1 as the antigen. Thus, T cells isolated from the blood of a subject may be cultured in the presence of FA1 for several days, such as for 5 days, after which a radioactive marker such as $^3$H-thymidine is added, and incorporation of the marker by the T cells is measured by scintillation counting.

In this embodiment, FA1 may conveniently be reacted with T cells of a sample taken from a subject to be diagnosed for preclinical IDDM. The sample may suitably be blood (serum) or a tissue sample, such as a pancreatic or lymph node sample. Alternatively, the T cells may be T cell clones isolated from the blood or tissue of the subject, e.g. as described in WO 91/17186.

Peptide sequences corresponding to full-length or partial T-cell receptor(s) reacting with FA-1 may be used as antigens to generate antibodies which may then be used to block the T-cell response recognising FA-1, thereby blocking the immune reponse of the T cells against FA-1. Alternatively, such antibodies, directed against FA-1 T-cell receptor peptide sequences can be used as diagnostic agents themselves to determine if T-cells reactive with FA-1 are present in a given individual, e.g. by means of immunohistochemistry, FACS analysis, immunopreciititation analysis, Western blotting analysis, or ELISA analysis with T-cells/lymphocytes. PCR analysis of (c)DNA isolated from lymphocytes using primers corresonding to fragment(s) of a DNA sequence encoding a given T cell receptor recognising FA1 may also be used to determined if T-cells reactive with FA-1 are present in a given individual.

T cell response to FA1 may also be measured in a cytotoxicity assay in which target cells expressing FA1 (either inherently or because they have been transfected with a DNA sequence coding for FA1) are labelled with a radioisotope, e.g. $^{51}$Cr, or a fluorescent label incorporated in the cells. Effector cells (T cells) are then incubated with the target cells. If the target cells are killed upon such contact, the radioisotope or fluorescent label is released from the cells and may be detected in the incubation media. Cytokine profiles may be measured in the T-cell assay in order to determine T-cell activity, e.g. gamma interferon, IL-10, IL-2, IL-12 and IL-4 (e.g. as described Romagnani et al., *Immunol. Today* 13, 1992, pp. 379–81). The T-cell reactivity can also be characterized using light microscopy.

In a particular embodiment of the present method, FA1 may be administered subcutaneously to the subject and any skin reaction at the site of administration is subsequently detected, such skin reaction being indicative of a T cell response to FA1.

The skin reaction may be visible as a localized reddening or swelling of the skin at the site of administration, e.g. as described in T. M. Kündig et al., *Proc. Nati. Acad. Sci. USA* 89, 1992, pp. 7757–7761. For this purpose, a composition comprising FA1 together with a suitable diluent or carrier may be prepared. Such a composition may conveniently be in the form of an injectable preparation containing FA1 dissolved or suspended in a suitable diluent such as isotonic saline. For use in the test, this preparation may be injected directly under the skin of the patient.

In the method according to the invention of determining the presence of FA1 autoantibodies in serum, the serum sample may conveniently be contacted with FA1 immobilized on a solid support, after which the solid support is contacted with a labelled reagent capable of binding to any autoantibody bound to the FA1, detection of any label bound to the solid support indicating the presence of FA1 autoantibodies in the sample.

The FA1 may be immobilized directly on the solid support by physical adsorption or be bound covalently or through bridging molecules such as protein A, polylysine or an antibody (preferably reactive with an epitope of FA1 which does not participate in binding the FA1 autoantibodies) to the solid support. The solid support employed in the method and test kit of the invention preferably comprises a polymer. The polymer may be selected from the group consisting of a plastic (e.g. latex, a polystyrene, polyvinylchloride, polyurethane, polyacrylamide, polyvinylalcohol, nylon, polyvinylacetate, and any suitable copolymer thereof), cellulose (e.g. various types of paper, such as nitrocellulose paper and the like), a silicon polymer (e.g. siloxane), a polysaccharide (e.g. agarose or dextran), or an ion exchange resin (e.g. conventional anion or cation exchange resins).

The physical shape of the solid support is not critical, although some shapes may be more convenient than others for the present purpose. Thus, the solid support may be in the shape of a plate, e.g. a microtiter plate, or a paper strip, dipstick, membrane (e.g. a nylon membrane or a cellulose filter) or solid particles (e.g. latex beads).

The labelled reagent used in the method and test kit of the invention may be an antibody reactive with the FA1 autoantibody (e.g. an anti-human antibody) including an anti-idiotype antibody (i.e. an antibody directed against the epitope-binding site of the FA1 autoantibody). The labelled reagent may also be a T-cell receptor for the FA1 autoantibody or a fragment thereof capable of binding to the FA1 autoantibody.

The label substance for the reagents used for binding to the FA1 autoantibody is preferably selected from the group consisting of enzymes, coloured or fluorescent substances and radioactive isotopes.

Examples of enzymes useful as label substances are peroxidases (such as horseradish peroxidase), phosphatases (such as acid or alkaline phosphatase), $\beta$-galactosidase, urease, glucose oxidase, carbonic anhydrase, acetylcholinesterase, glucoamylase, lysozyme, malate dehydrogenase, glucose-6-phosphate dehydrogenase, $\beta$-glucosidase, proteases, pyruvate decarboxylase, esterases, luciferase, etc.

Enzymes are not in themselves detectable but must be combined with a substrate to catalyse a reaction the end product of which is detectable. Thus, a substrate may be added after contacting the support with the labelled reagent, resulting in the formation of a coloured or fluorescent substance. Examples of substrates which may be employed according to the invention include hydrogen peroxide/ tetramethylbenzidine or chloronaphthole or o-phenylenediamine or 3-(p-hydroxyphenyl) propionic acid or luminol, indoxyl phosphate, p-nitrophenylphosphate, nitrophenyl galactose, 4-methyl umbelliferyl-D- galactopyranoside, or luciferin.

Alternatively, the label substance may comprise coloured or fluorescent substances, including gold particles, coloured or fluorescent latex particles, dye particles, fluorescein, phycoerythrin or phycocyanin.

Radioactive isotopes which may be used for the present purpose may be selected from I-125, I-131, H-3, P-32, P-33 and C-14.

In an alternative embodiment, the serum sample may be contacted with FA1 immobilized on a solid support simultaneously with contacting the immobilized FA1 with a predetermined amount of a labelled antibody competing with the autoantibody for binding to FA1, detection of any decrease in the amount of labelled antibody bound to the solid support relative to the amount of labelled antibody added indicating the presence of FA1 autoantibodies in the sample.

In this case, the labelled antibody is suitably one which is reactive with the epitope of FA1 which binds the FA1 autoantibody. Thus, the antibody may be one which is raised against a peptide fragment comprising this epitope.

In this embodiment, the solid support and label substance may be as described above.

The antibody raised against a peptide fragment of FA1 may conveniently be used in the method and test kit of the invention as the labelled reagent, labelled antibody or antibody immobilized on the solid support to which the FA1 is subsequently bound, as indicated above. In the present context, the term "antibody" is used to indicate any substance formed in the human or animal body or by a human or animal cell as a response to exposure to the antigen. The antibody may be a polyclocal or monoclonal antibody or may be one prepared by recombinant DNA techniques. The term also includes antibody fragments, such as Fab', F(ab')$_2$ or Fv fragments as well as single-domain antibodies.

Monoclonal antibodies may be obtained by well-established methods, e.g. as described in A. Johnstone and R. Thorpe, *Immunochemistry in Practice*, 2nd. Ed., Blackwell Scientific Publications, 1987, pp. 35–43. When prepared by recombinant DNA techniques, the antibody may be produced by cloning a DNA sequence coding for the antibody or a fragment thereof into a suitable cell, e.g. a microbial, plant, animal or human cell, and culturing the cell under conditions conducive to the production of the antibody or fragment in question and recovering the antibody or fragment thereof from the culture. Possible strategies for the preparation of cloned antibodies are discussed in, for instance, L. Riechmann et al., *Nature* 332, Mar. 24, 1988, p. 323 ff., describing the preparation of chimeric antibodies of rat variable regions and human constant regions; M. Better et al., *Science* 240, May 20, 1988, p. 1041 ff., describing the preparation of chimeric mouse-human Fab fragments; A. Sharra and A. Plückthun, *Science* 240, May 20, 1988, pp. 1038–1040, describing the cloning of an immunoglobulin Fv fragment containing antigen-binding variable domains; and E. S. Ward et al., *Nature* 341, Oct. 12, 1989, pp. 544–546, describing the cloning of isolated antigen-binding variable domains ("single-domain antibodies").

The peptide fragment against which the antibody is raised may be prepared by conventional peptide synthesis using a device available from Applied Biosystems as described in D. Atar et al., *J. Immunol.* 143, 1989, pp. 533–538.

In particular for use as the labelled reagent or as the antibody immobilized on the solid support, the antibody is advantageously one which is raised against an epitope of FA1 which does not participate in binding autoantibodies so as not to interfere with the binding of any FA1 autoantibodies present in the sample or so as to ensure optimal binding of the labelled reagent to any FA1 autoantibodies bound to FA1 in the assay.

If, on the other hand, the antibody is intended for use as the labelled antibody competing with any antibodies in the sample for binding to the immobilized FA1, the antibody is preferably one which is raised against an epitope of FA1 which binds the FA1 autoantibody.

DESCRIPTION OF SPECIFIC EMBODIMENTS OF THE DIAGNOSTIC METHOD

In one embodiment, the test kit of the invention comprises, in separate containers, (a) fetal antigen 1 (FA1) immobilized on a solid support, and (b) a labelled reagent capable of binding to the FA1 autoantibody.

In this case, the FA1 may be bound to an antibody immoblised to the solid support, as indicated above. The labelled reagent is preferably an antibody.

In another embodiment, the test kit of the invention comprises, in separate containers, (a) an antibody reactive with an epitope of FA1 which does not participate in binding the autoantibodies, the antibody being immobilized on a solid support, (b) FA1, and (c) a labelled reagent capable of binding to the autoantibody.

In a further embodiment, the test kit of the invention comprises, in separate containers, (a) fetal antigen 1 (FA1) immobilized on a solid support, and (b) a labelled antibody which is capable of competing with the FA1 autoantibody for binding to FA1.

The labelled antibody may be one which is raised against a peptide fragment of FA1.

The FA1 may be bound to an antibody immobilized on the solid support, as indicated above.

In a still further embodiment, the test kit of the invention comprises, in separate containers, (a) an antibody reactive with an epitope of FA1 which epitope does not participate in binding the FA1 autoantibodies, the antibody being immobilized on a solid support, (b) FA1, and (c) a labelled antibody which is capable of competing with the autoantibody for binding to FA1.

It is at present contemplated that the FA1 may have a therapeutic use. Thus, it is believed to be of potential use in a method of preventing the development of IDDM, in which method FA1 or a fragment thereof is administered to an individual who does not show clinical symptoms of IDDM in a quantity sufficient to induce immunological tolerance to FA1. It is also possible that administration of FA1 may be used to treat preclinical IDDM or to ameliorate early clinical IDDM.

The proposed therapeutic use of FA1 is based on similar attempts to provide immunotherapy of IDDM with other antigens.

Immunotherapy with glutamic acid decarboxylase ($GAD_{65}$, the smaller isoform) in animal models of IDDM has been demonstrated by several groups (Kaufman et al., *Nature* 366, 1993, pp. 69–72, Tisch et al., *Nature* 366, 1993, pp. 72–75, Petersen et al., *Diabetes* 43 1994, pp. 1478–84 and Elliott et al., *Diabetes* 43, 1994, pp. 1494–99). By injecting recombinant $GAD_{65}$ intravenously into 3 week-old non-obese-diabetic (NOD) mice, Kaufman et al. have completely prevented development of IDDM as well as islet autoimmunity, i.e. mononuclear cell infiltration in the islets (insulitis). By injecting recombinant $GAD_{65}$ into the thymus of 3 week-old non-obese-diabetic (NOD) mice, Tisch et al. have prevented/delayed the development of IDDM as well as islet autoimmunity, i.e. mononuclear cell infiltration in the islets (insulitis). By injecting $GAD_{65}$ affinity purified from rat brains intraperitoneally into neonatal (24h) non-obese-diabetic (NOD) mice, Petersen et al. have prevented/delayed the development of IDDM as well as islet autoimmunity, i.e. mononuclear cell infiltration in the islets (insulitis). By immunizing NOD mice once with $GAD_{67}$ (the larger isoform), Elliott et al. have completely prevented the onset of clinical diabetes.

Furthermore, insulin therapy in animal models of IDDM (Gotfredsen et al., *Diabetologia* 28, 1985, pp. 933–35 and Ackinson et al., *Diabetes* 39, 1990, pp. 933–37) as well as in humans at high risk of disease (Keller et al., *Lancet* 341, 1993, pp. 927–28) has also been demonstrated to delay/prevent the onset of diabetes. Keller et al. have demonstrated that low doses of subcutaneous insulin can delay/prevent the onset of clinical IDDM in individuals at high risk of developing the disease. Likewise, in both the BB-rat (Gotfredsen et al.) and in the NOD mice (Ackinson et al.) prophylactic insulin therapy have been demonstrated to prevent/delay the onset of clinical diabetes. H. Zhang et al. (*Proc Natl Acad.* 88, pp. 10252–56) have also demonstrated that oral insulin therapy in NOD mice delays/prevents the onset of IDDM as well as insulitis.

Based on these data, it is suggested that FA1 administered by injection with or without adjuvant or orally, can be used in immunotherapy of IDDM in individuals at risk of developing the disease, or in recent onset IDDM patients in order to inhibit/prevent the autoimmune β-cell destruction.

The dosage of FA1 administered to a patient will vary with the type and severity of the condition to be treated, as well as the form of administration (e.g. oral or intravenous), but is generally in the range of 100–1000 mg per day for about 1 year (for oral administration).

To this end, the present invention provides a pharmaceutical composition for preventing or treating preclinical IDDM or for ameliorating early clinical IDDM, the composition comprising fetal antigen 1 together with a pharmaceutically acceptable diluent or carrier.

In the pharmaceutical composition of the invention, the FA1 may be formulated by any of the established methods of formulating pharmaceutical compositions, e.g. as described in *Remington's Pharmaceutical Sciences*, 1985. The composition may be in a form suited for systemic injection or infusion and may, as such, be formulated with sterile water or an isotonic saline or glucose solution. The composition may be sterilized by conventional sterilization techniques which are well known in the art. The resulting aqueous solutions may be packaged for use or filtered under aseptic conditions and lyophilized, the lyophilized preparation being combined with the sterile aqueous solution prior to administration. The composition may contain pharmaceutically acceptable auxiliary substances as required to approximate physiological conditions, such as buffering agents, tonicity adjusting agents and the like, for instance sodium acetate, sodium lactate, sodium chloride, potassium chloride, calcium chloride, etc.

The pharmaceutical composition of the present invention may also be adapted for oral, nasal, transdermal or rectal administration. The pharmaceutically acceptable carrier or diluent employed in the composition may be any conventional solid carrier. Examples of solid carriers are lactose, terra alba, sucrose, talc, gelatin, agar, pectin, acacia, magnesium stearate and stearic acid. Similarly, the carrier or diluent may include any sustained release material known in the art, such as glyceryl monostearate or glyceryl distearate, alone or mixed with a wax. For oral administration, the composition may be tabletted, placed in a hard gelatin capsule in powder or pellet form or it can be in the form of a troche or lozenge. The amount of solid carrier will vary widely but will usually be from about 25 mg to about 1 g. The FA1 may also be placed in a soft gelatin capsule in a liquid carrier such as syrup, peanut oil, olive oil or water.

The present invention is further illustrated by the following example which is not in any way intended to limit the scope of the invention as claimed.

EXAMPLE

Radioiodination of FA1

200–300 μl of purified FA1 (about 150 μg, purified by immunospecific affinity chromatography as described by C. H. Jensen et al., *Human Reprod*. 8, 1993, pp. 635–641, were transferred to glass ampoules precoated with 20 ng iodogen. 4 μl $^{125}I$ (specific activity 100 mCi/ml, available from Amersham International) was added and iodination performed during agitation at room temperature for 15 minutes. Labelled protein was isolated on PD10 columns (Sephadex G 25, available from Pharmacia) preequilibrated and run with 0.2% (v/v) NP40 in PBS, and 600 µl fractions were collected. These fractions were analysed by trichloroacetic acid (TCA precipitation.

To 2 µl of each fraction obtained above, 1 ml 10% (w/v) TCA and 1 ml 0.1% (w/v) BSA in PBS were added. The samples were incubated on ice for 15–30 minutes and centrifuged at 1500×g for 10 minutes. 2 µl supernatant was saved and analysed in a gamma scintillation couter together with the pellet and 2 µl of the original fraction. The top fraction was identified, and the iodinated FA1 was further purified by size chromatography.

Detection of Autoantibodies Against FA-1

COS-7 cells were transfected with DNA encoding FA-1 in a manner described previously (B. Michelsen et al., *Proc. Natl. Acad. Sci. USA* 88, 1991, pp. 8754–8758) and labelled with 5 mCi $^{35}$S-cystine in 10 ml of medium containing 20×10$^6$ transfected COS-7 cells of for 4 h at 37° C. After labelling, the transfected COS-7 cells were swollen on ice for 10 min in 10 mM HEPES, pH 7.4, 1 mM MgCl$_2$ and 1 mM EGTA and homogenized using a Polytron speed 4 for 2×40 sec. The cell homogenate was then centrifuged for 10 min at 3000 rpm. The supernatant from the transfected COS-7 cells was used in immunoprecipitation analysis. Supernatant from approximately 1×10$^6$ cells was incubated with 20 µl of serum from either IDDM patients or healthy controls for 16 h at 4° C. to form immunocomplexes. The immunocomplexes were isolated by absorption to Protein A-Sepharose (PAS) (Pharmacia, Sweden) (1 mg/µl serum). Following washing, the PAS pellets were boiled for 3 min. in 1 M Tris, 60% v/v sucrose, 15% w/v SDS, 0.01% w/v bromophenol blue, pH 6.8, with 1% β-mercaptoethanol, centrifuged and the supernatant subjected to analysis by 10% SDS-PAGE. After drying, the gel-immunoprecipitated FA-1 was detected on gels by fluorography. 64% (9 of 14) of recent onset IDDM patients showed antibody reactivity against FA-1 expressed in COS-7 cells, in contrast to 0% (0 of 5) healthy controls.

Detection of T-cell Reactivity Against FA-1

Figure 2:
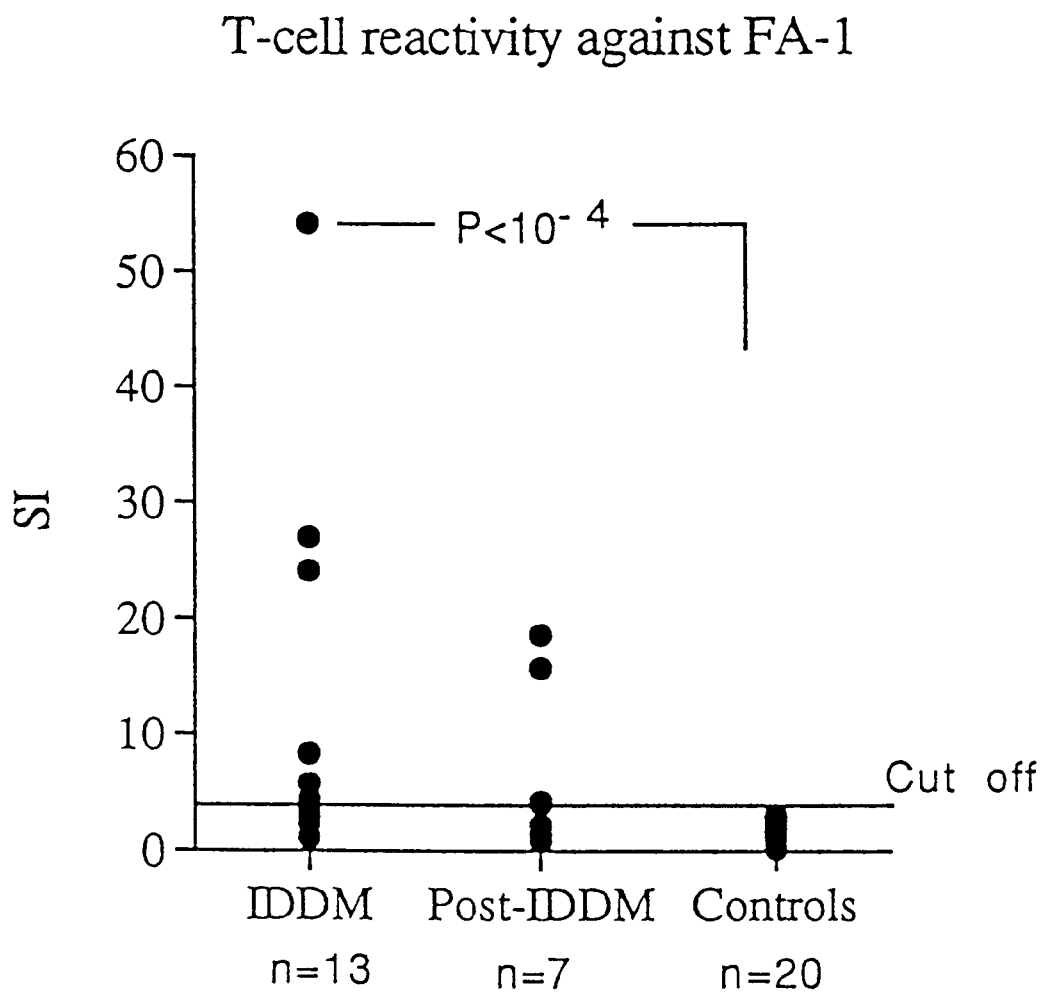
FIG. 2 is a graphic illustration of reactivity against FA-1 of T cells derived from control patients, newly diagnosed IDDM patients, and post-IDDM patients (mean duration of IDDM, 4.5 years).

Peripheral blood mononuclear cell (PBMC) were isolated by Ficoll-Metratrizoate density gradient centrifugation from freshly drawn heparinized blood from recent onset IDDM patients, patients with established IDDM and healthy controls. 150,000 PBMC were cultured in tissue-coated, round-bottom 69-well plates (Costar, Cambridge, Mass.) for 5 days at 37° C., 5% CO2, in 150 µl Iscove's modified Dulbecco's medium with 2 mM glutamine (Gibco, Paisley, Scotland), supplemented with 10% human type AB pool serum, 10 U/ml penicillin and 10 µg/ml streptomycin (Flow Laboratories, Irvine, Scotland), in the presence of either affinity purified human FA-1 antigen 0–25 µg/ml or tetanus toxoid (1.5 Lf/ml) or in medium alone. After 5 days, 50 µl RPMI 1640 (Gibco) containing 0.5 µCi $^3$H-thymidine was added per well, and the incubation was continued for 16 hours. Cultures were then harvested on glass-fibre filters and $^3$H-thymidine incorporation was measured by liquid scintillation counting. The results are expressed as stimulation indices (cpm in the presence of antigen divided by cpm in absence of antigen). Only incubations resulting in SI index above 3.0 were considered positive. 77% (10 of 13) of the recent onset IDDM patients were positive compared to 0% (0 of 20) of the controls ((FIG. 2) $P<10^{-4}$. Furthermore, 57% (4/7) of IDDM patients with a mean duration of IDDM of 4.5 years were positive (Post-IDDM) (FIG. 2).

We claim:

1. A method of diagnosing preclinical insulin-dependent diabetes mellitus (IDDM), comprising contacting fetal antigen 1 (FA1) with T cells of a subject to be diagnosed for preclinical IDDM and detecting any T cell response to the FA1, such a response being indicative of preclinical IDDM in the subject.

2. A method according to claim 1, wherein the T cells are clones derived from T cells isolated from the blood or tissue of the subject.

3. A method according to claim 1, wherein said T cell response is detected using a method selected from the group consisting of: (i) detecting induction of T cell proliferation by FA1; (ii) detecting reactivity of T cells with antibodies that specifically recognize FA1-specific T cells; (iii) detecting the presence of nucleic acid encoding FA1-specific T cell receptor; (iv) detecting the ability of T cells to kill FA1-containing effector cells; and (v) detecting a skin reaction in the subject at the site of subcutaneous administration of FA1.

4. A method according to claim 1, wherein the FA1 is human FA1.

5. A method of determining the presence of autoantibodies against fetal antigen 1 (FA1 autoantibodies) in serum, comprising contacting a human serum sample with FA1 or a fragment thereof capable of binding FA1 autoantibodies, and detecting any binding of human autoantibodies to the FA1.

6. A test kit for determining the presence of fetal antigen 1 autoantibodies (FA1 autoantibodies) in human serum, which comprises, in separate containers, (a) FA1 immobilized on a solid support, and (b) a labelled reagent capable of binding to human FA1 autoantibodies.

7. A test kit according to claim 6, wherein the labelled reagent is an antibody.

8. A test kit according to claim 6, wherein the FA1 is human FA1.

* * * * *